(12) United States Patent
Wu et al.

(10) Patent No.: US 11,871,082 B2
(45) Date of Patent: Jan. 9, 2024

(54) METHODS AND APPARATUS FOR MEDIA PLAYBACK BASED ON CUE POINTS

(71) Applicant: MTFITNESSPAL, INC., San Francisco, CA (US)

(72) Inventors: Gloria Wu, Austin, TX (US); Scott Laing, Austin, TX (US); Lauren McKenna, Austin, TX (US)

(73) Assignee: MyFitnessPal, Inc., Austin, TX (US)

( * ) Notice: Subject to any disclaimer, the term of this patent is extended or adjusted under 35 U.S.C. 154(b) by 0 days.

(21) Appl. No.: 16/730,900

(22) Filed: Dec. 30, 2019

(65) Prior Publication Data

US 2021/0204030 A1 Jul. 1, 2021

(51) Int. Cl.
| | |
|---|---|
| *H04N 7/173* | (2011.01) |
| *H04N 21/472* | (2011.01) |
| *A63B 24/00* | (2006.01) |
| *H04N 21/422* | (2011.01) |

(52) U.S. Cl.
CPC ... *H04N 21/47217* (2013.01); *A63B 24/0075* (2013.01); *H04N 21/42224* (2013.01); *H04N 21/47202* (2013.01)

(58) Field of Classification Search
CPC ....... H04N 21/47217; H04N 21/47202; H04N 21/42224; A63B 24/0075
See application file for complete search history.

(56) References Cited

U.S. PATENT DOCUMENTS

| | | | |
|---|---|---|---|
| 9,526,946 B1* | 12/2016 | Zets | A61B 5/6892 |
| 9,842,507 B1* | 12/2017 | Borenstein | G06K 9/00765 |
| 2008/0077620 A1* | 3/2008 | Gilley | A63B 22/02 |
| 2008/0086318 A1* | 4/2008 | Gilley | G16H 10/20 |
| | | | 705/319 |
| 2010/0216098 A1* | 8/2010 | Montgomery | G09B 19/0092 |
| | | | 434/127 |
| 2010/0313768 A1* | 12/2010 | Koether | A47J 36/321 |
| | | | 99/325 |
| 2011/0103766 A1* | 5/2011 | Priddle | H04N 21/845 |
| | | | 386/241 |
| 2011/0182425 A1* | 7/2011 | Burnett | H04N 21/4408 |
| | | | 380/200 |
| 2013/0239146 A1* | 9/2013 | Cherry | H04N 21/482 |
| | | | 725/43 |
| 2014/0033050 A1* | 1/2014 | Shin | H04N 21/4788 |
| | | | 715/733 |
| 2014/0137170 A1* | 5/2014 | Molinelli | H04N 21/47202 |
| | | | 725/93 |
| 2015/0032959 A1* | 1/2015 | Gupta | G06F 11/3051 |
| | | | 711/118 |

(Continued)

*Primary Examiner* — Annan Q Shang
(74) *Attorney, Agent, or Firm* — Maginot, Moore & Beck, LLP

(57) ABSTRACT

Systems, apparatus, and methods for media playback based on cue points. Various embodiments of the present disclosure are directed to instructional media components (e.g., video, audio, and/or text) that focus the user's attention on details of proper form. The cue point navigation system enables the user to navigate the instructional media according to specific movement cues. Notably, the UI minimizes navigational complexity, while simultaneously maximizing user comprehension. As described in greater detail herein, hybrid media playback advantageously provides the user with different ways to absorb the instructional information.

18 Claims, 8 Drawing Sheets

(56) References Cited

U.S. PATENT DOCUMENTS

| | | | |
|---|---|---|---|
| 2015/0195601 A1* | 7/2015 | Hahm | H04N 21/47202 |
| | | | 725/116 |
| 2017/0025039 A1* | 1/2017 | Oguchi | G09B 5/065 |
| 2017/0263147 A1* | 9/2017 | King | G11B 27/026 |
| 2018/0199110 A1* | 7/2018 | Cormican | G06F 3/04817 |
| 2019/0295438 A1* | 9/2019 | Rubinstein | G09B 5/06 |
| 2020/0084507 A1* | 3/2020 | Prestegard | H04N 21/8451 |
| 2021/0228022 A1* | 7/2021 | Liu | F24C 7/081 |

* cited by examiner

METHODS AND APPARATUS FOR MEDIA PLAYBACK BASED ON CUE POINTS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This disclosure relates generally to the field of media playback. More particularly, the present disclosure relates to systems, computer programs, devices, and methods for instructional media playback.

DESCRIPTION OF RELATED TECHNOLOGY

Ready access to the Internet has revolutionized how people gather information and learn. The modern consumer is more likely to self-educate with online videos, than consult face-to-face with professionals. As but one such example, many people go online to learn exercises and workouts rather than paying for a personal trainer.

Unfortunately, certain types of exercises are difficult to learn. Nuances such as e.g., timing, coordination, and movement may require significant skill to execute properly. Without the assistance of a personal trainer to correct poor form, an athlete may develop bad habits and suffer from injury and/or reduced performance progression.

SUMMARY

The present disclosure addresses the foregoing needs by disclosing, inter alia, methods, devices, systems, and computer programs for providing instructional media playback according to cue points, thereby enabling users to focus on specific portions of interest.

In one aspect, a user apparatus is disclosed. In one embodiment, the user apparatus includes: a user interface; a network interface; a processor; and a non-transitory computer-readable medium. In one exemplary embodiment, the non-transitory computer-readable medium includes one or more instructions, which when executed by the processor, causes the user apparatus to: obtain instructional media, where the instructional media comprises a plurality of cue points associated with a plurality of media components of the instructional media; obtain user selection of a first cue point; and render a first media component of the instructional media, wherein the first media component is associated with the first cue point.

In one variant, the one or more instructions when executed by the processor further causes the user apparatus to: display a plurality of text descriptions associated with the plurality of cue points; wherein the user selection of the first cue point comprises a hit within a hit box of a first text description.

In one variant, the plurality of media components are video frames and the plurality of cue points are timestamps.

In one variant, the plurality of media components are video files and the plurality of cue points are file handles.

In one variant, the one or more instructions when executed by the processor further causes the user apparatus to: obtain a second user selection of a second cue point; where a second media component is associated with the second cue point; and render the first media component and the second media component in sequence.

In one variant, the one or more instructions when executed by the processor further causes the user apparatus to: obtain a second user selection of a second cue point; where a second media component is associated with the second cue point; and render the first media component and the second media component concurrently. In one such variant, the user apparatus also includes a hardware codec and the first media component is rendered via the hardware codec, and the second media component is rendered via a software process.

In one aspect, a method for rendering hybrid media based on cue point navigation is disclosed. In one embodiment, the method includes: displaying a plurality of text descriptions of a plurality of movement cues via a touch screen interface; responsive to a user selection of at least one text description: retrieving a reference data structure from a table of contents data structure; de-referencing the reference data structure to identify a video segment in an instructional media data structure; and playing the video segment via the touch screen interface.

In one variant, de-referencing the reference data structure to identify the video segment in the instructional media data structure is further based on one or more user personalization data.

In one variant, the method further includes de-referencing the reference data structure to identify an audio snippet; and playing the audio snippet via a speaker of a client device, concurrent with the video segment. In one such variant, de-referencing the reference data structure to identify the audio snippet in the instructional media data structure is further based on one or more user personalization data.

In one variant, the method includes de-referencing the reference data structure to identify a link to personalized media residing on a server; and retrieving the personalized media for playback, concurrent with the video segment.

In one variant, the method includes de-referencing the reference data structure to identify a local media residing on a user device; and retrieving the local media for playback, concurrent with the video segment.

In one variant, the method further includes responsive to a second user selection of a second text description: retrieving a second reference data structure from the table of contents data structure; de-referencing the second reference data structure to identify a second video segment in the instructional media data structure; and playing the video segment and the second video segment concurrently via the touch screen interface.

In one aspect, a method for providing instructional media based on cue points is disclosed. In one embodiment, the method includes: obtaining an instructional media comprising multiple media components and a table of contents data structure; indexing the instructional media according to one or more cue points; generating a workout plan for a user; and providing a subset of the instructional media and the workout plan to a client device associated with the user.

In one variant, the subset of the instructional media is selected based on a workout history of the user.

In one variant, the subset of the instructional media is selected based on a personalization option of the user.

In one variant, the subset of the instructional media is selected based on a user interface of the client device.

In one variant, the subset of the instructional media comprises a link to 3$^{rd}$ party media components associated with the user.

In one variant, the instructional media is obtained from a population of users.

More generally, various aspects of the present disclosure are directed to systems, apparatus, methods and storage media which enable instructional media navigation and playback in common fitness environments. Specifically, the described system and method enables users to focus on specific portions of interest using cue point navigation.

Other features and advantages of the present disclosure will immediately be recognized by persons of ordinary skill in the art with reference to the attached drawings and detailed description of exemplary embodiments as given below.

Figure 1A:
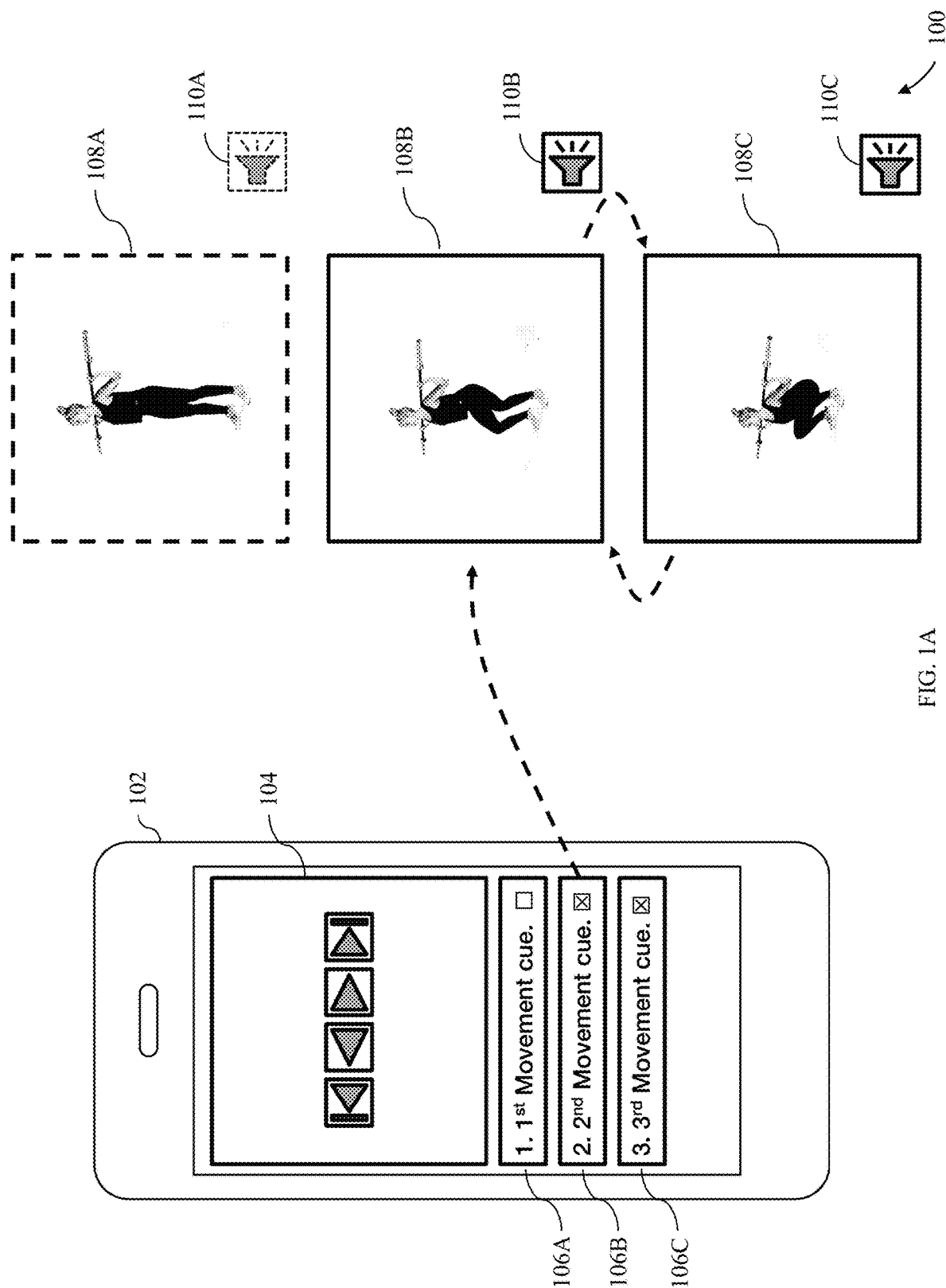
FIG. 1A is a graphical representation one exemplary user interface (UI) configured to playback hybrid exercise media according to movement cue points, consistent with the various principles described herein.

All Figures © Under Armour, Inc. 2019. All rights reserved.

DETAILED DESCRIPTION

Disclosed embodiments include systems, apparatus, methods and storage media which provide instructional media playback according to cue points.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without departing from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Similar logic applies to the use of the term "or" herein; i.e., "A or B" means (A), (B), or (A and B).

The terms "comprising," "including," "having," and the like, as used with respect to embodiments of the present disclosure, are synonymous.

The Importance of Proper Form

Many physical exercises are associated with specific sequences of movements (also commonly referred to as "form"). Proper form ensures that the body maximizes its load carrying capability throughout the complete range of motion of the exercise. Improper form expends unnecessary energy and/or increases muscular strain to compensate for the less efficient motion. Form directly impacts exercise and/or workout effectiveness. Improper form can increase the likelihood of injury, reduce the exercise's effectiveness on primary muscle groups, increase strain on secondary muscle groups, and/or cause earlier fatigue.

Unfortunately, the dynamic nature of exercises can be very difficult to describe in words. For example, a text-based description of a squat might be summarized with the following steps:

Walk up to the bar and grab it with your hands six inches wider than shoulder-width apart. Duck under the bar and rest it on your upper back. Make sure it's not pressing into your spine. Stand up to clear the bar from the rack and take a step back to give yourself room.

Set your feet wherever you're most comfortable and squat down. Keep your feet flat the entire time, your heels should never come off the ground. Squat down as low as you can while keeping your back straight, then stand up. Try to look straight forward the whole time, never down or up.

While the foregoing text is informative, it cannot capture every nuance of form. For example, different people have different sizes and dimensions; terms such as "upper back" and "shoulder-width" are generic enough to be understood by the population at large, but imprecise. Similarly, while experienced athletes might understand technical descriptions of movements, neophytes may find such terminology confusing and/or misinterpret the instruction. Furthermore, certain types of exercise require fluid coordination between multiple muscle groups (e.g., kettle bell swings, snatch, clean and jerk, etc.); text-based descriptions are better suited for static states, rather than fluid movement.

As previously alluded to, many users prefer learning from instructional videos. Video readily expresses dynamic movement and biomechanical positioning e.g., a user can view a video of a squat and easily understand where barbell placement should generally be relative to their anatomy, approximately how low they should be squatting, and how the squat movement can be fluidly performed, etc.

Unfortunately, while video has some advantages over text, it is not without its own disadvantages. Video is contiguous in time i.e., video playback occurs sequentially at a default rate (e.g., 24 fps, 30 fps, 60 fps, etc.). While some rendering devices offer skip-to, fast forward, slow-motion, and rewind navigation, often these capabilities assume a specific user interface (e.g., touch screen and/or mouse). This can be particularly problematic for fitness applications which must work in a variety of settings (e.g., most consumer electronics are not designed to be struck, dropped, or subjected to the harsh elements (rain, water, etc.)) As but one such example, capacitive touchscreen granularity can be heavily affected by foreign substances (such as sweat, saliva, and chalk) on fingertips. Attempting to navigate to a specific point in a video using slider bars on a capacitive touchscreen mid-workout can be frustratingly inaccurate.

Furthermore, video is contiguous in space (visual perspective); framing video to capture a three-dimensional (3D) subject can be tricky. Consider the aforementioned squat: framing a person standing in an upright position (front view), holding a barbell on their upper-back (back view), with their feet at shoulder-width (top view), requires multiple vantage points to completely describe. The highest quality instructional videos require a significant production team that carefully plan out shots and videography. High cost production is a significant barrier to content creation.

Finally, video is contiguous in subject matter. Often times, instructional videos are shot once with a single model (typically a male of a specific age, height, weight, and musculature). However, single subject videography is poorly suited to the modern commercial climate; there are significant benefits to inclusively supporting many different body types (e.g., gender, age, height, weight, musculature, ethnicity, accessibility, etc.)

The complexities of exercise form and the limitations of videography can result in user confusion and improper form. For example, a user may unintentionally navigate past (or mistakenly ignore) important information. In some scenarios, navigation errors are most likely to occur mid-workout i.e., right before the user attempts the exercise. Furthermore, a user may not be able to see full range of motion and/or positioning from the video vantage point. Also, a user may want or need accommodation based on their body type; for example, a tall user may need different instructions than a short user, a wheelchair user may need accessibility modifications, etc.

More directly, while video remains an important component of fitness education, there exists a persistent need for user-controllable focus within the instructional content.

Example Operation

As a brief aside, the Assignee hereof has historically emphasized (e.g., in educational materials, literature and publications) the importance of "movement cues" for various exercises. A movement cue provides athletes with criteria for evaluating execution quality (e.g., form), at various points within the context of a broader exercise. Movement cues explicitly focus an athlete's attention on the elements of correct form, thereby facilitating the learning process. For example, the movement cue for a squat motion might identify an ideal range of foot positioning and angles, etc.

Various embodiments of the present disclosure combine the concept of movement cues with media navigation. In one embodiment of the present disclosure, a library of exercise media is divided into segments according to movement cue points. For example, a movement cue may be demonstrated and/or described with video segments, audio snippets, and/or text descriptions. Notably, instructional media may be a hybrid combination of many different types of media. In one exemplary implementation, a hybrid media playback for each movement cue can be generated from the instructional media, based on a "table of contents" data structure for playback navigation. Each of the constituent media components is described by a reference data structure (e.g., a step identifier, a timestamp, a pointer, a file handle, etc.)

The exemplary library of exercise media is stored within a health and fitness network. The client device can select portions of the instructional media to render in a hybrid media display, based on user input. For example, a user may configure their device to render only video and text, audio and text, and/or another hybrid combination (based on e.g., user considerations (accessibility, age, gender, body type, etc.), device considerations (e.g., user interface types, available bandwidth/memory, etc.), and/or any other playback considerations.

In one embodiment, a user is prescribed workout plans as part of their health and fitness regimen. For instance, the user may have completed an initial "onboarding" program that identified the user's personal fitness goals and prescribed a workout plan. In one such variant, the onboarding information enables the health and fitness network to tailor instructional media for the user. As but one such example, the onboarding process may identify a library of exercise media based on e.g., exercises that fit the user's personal fitness goals, fitness models that match or otherwise appeal to the user (based on age, gender, body structure), etc.

FIG. 1A is a graphical representation one exemplary user interface (UI) 100 configured to playback hybrid exercise media according to movement cue points. As shown in FIG. 1A, the client device 102 includes a video player 104 and text boxes for each movement cue (106A, 106B, 106C). The user selects which movement cues should be played. The user selections correspond to reference data structures (e.g., timestamps) that may be retrieved from the table of contents data structure to enable playback of media components: e.g., video segments (108A, 108B, 108C) and corresponding audio snippets (110A, 110B, 110C).

In the illustrated embodiment, the user has requested an instructional "squat" video from a library of exercise videos. For instance, the user may have looked-up the squat exercise to focus on improving their technique. In another common scenario, the user may have been provided with the video the first time that the user was assigned the squat exercise.

The UI enables the user to select only a subset of instructional media for playback; in the illustrated example, the 2nd and 3rd movement cue points (106B, 106C) are selected to "loop" (the first movement cue point 106A is skipped). The textual descriptions 106A, 106B, 106C are displayed providing the user with a broad overview of all movement cues (even the skipped movement cue). Audio snippets 110B, 110C may accompany the segmented video playback 108B, 108C and provide the user with a detailed explanation of the movement cues. In this manner, the user can focus on the selected elements of correct form, while watching the model perform the squat movement.

Unlike existing instructional video playback, the movement cue point-based navigation system enables the user to: play (or reverse) instructional media according to specific movement cue points and skip ahead/back (in time or by cue points), etc. Notably, the UI enables quick navigation between movement cue points with only button presses; this is particularly important where there are confounding circumstances (e.g., where the user's hands may have sweat, chalk, saliva). In other variants, the UI may support audio commands e.g., for situations where the user does not have any free hands. More directly, instructional media (unlike general purpose entertainment media) is choreographed to convey specific information at specific points in time. Enabling the client device to selectively playback instructional media at these salient points minimizes UI requirements, while simultaneously maximizing user comprehension.

Additionally, hybrid media playback advantageously provides the user with different ways to absorb the instructional information. In this example, the user has both textual and audio descriptions of the movement cue, as well as video exemplars. Notably, workouts occur in a broad range of environments which may be better (or poorly) suited for certain media types. For example, workouts may be loud and noisy, in some cases audio instructions cannot be given or understood, thus text and video UIs may be preferred. In contrast, certain movements may require the user to look away from the screen (e.g., during a yoga pose, etc.); under such conditions, audio UIs may be much more effective. Still other types of media and/or UIs may be substituted e.g., haptic, accelerometers, motion sensing, and/or rumble box type interfaces may be incorporated into clothing, fabric, or other wearable type devices.

Figure 1B:
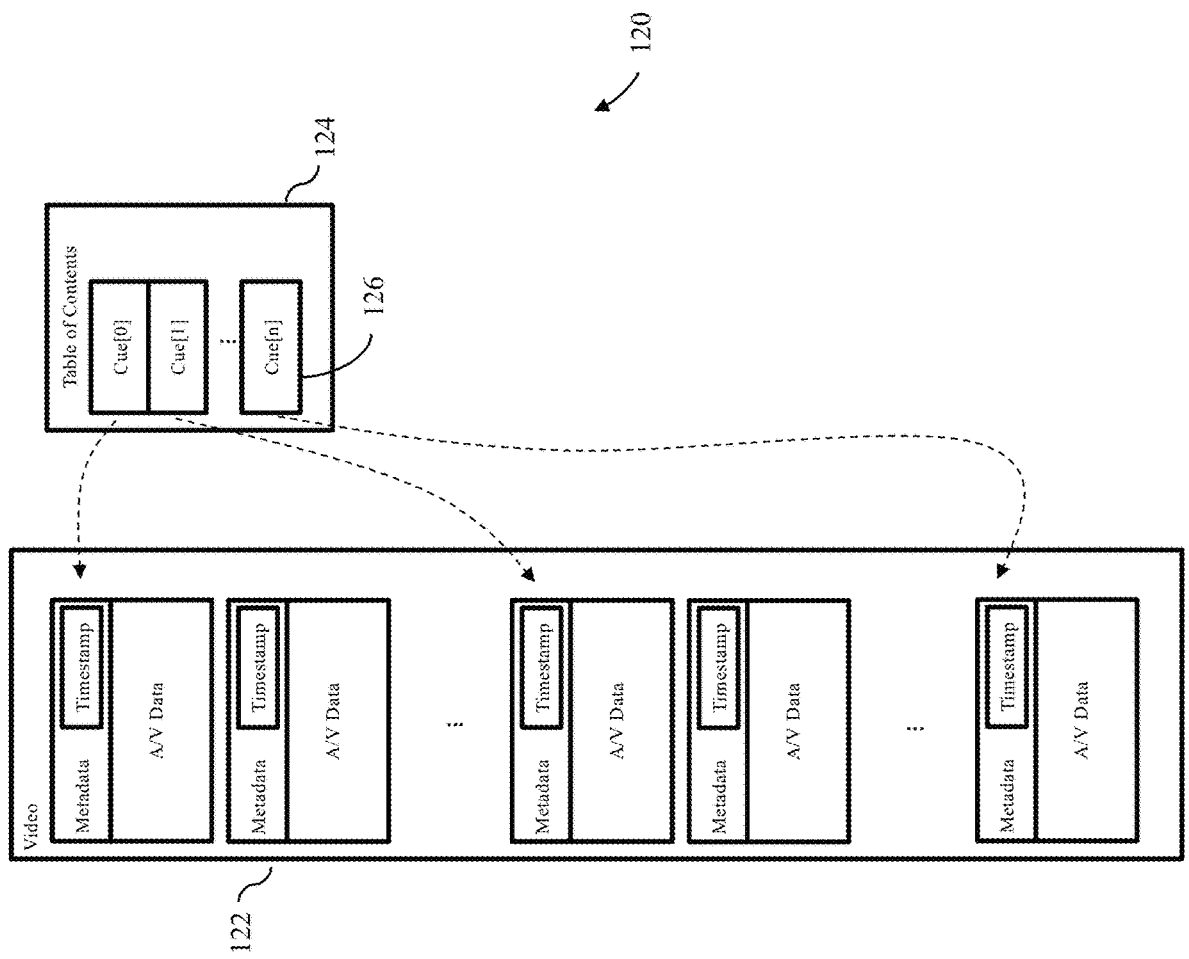
FIGS. 1B-1D are graphical representations of exemplary instructional media data structures, consistent with the various principles described herein.

Referring now to FIG. 1B, a graphical representation of one exemplary instructional media data structure 120 is depicted. As shown in FIG. 1B, the instructional media data structure 120 includes a video file 122 and a table of contents data structure 124. The video file 122 has been segmented in time according to movement cue points; the reference data structures 126 identify timestamps corresponding to the movement cue points. The instructional media data structure 120 may include video frame data, audio track data, and text overlays (e.g., stored within subtitle or close captioning metadata and/or as a separate track).

During playback operation, the client device provides a hybrid media rendering e.g., of text and video. For example, the client device may display the textual descriptions of the exercise to enable a user to quickly scan over different movement cues (e.g., text browser 106A, 106B, 106C of FIG. 1A). Notably, text is not limited by viewpoint (temporal, spatial continuity) in the same way that video and/or audio may be. The textual descriptions enable the user to identify portions of the exercise to focus on. For instance, the user may tap on a textual description of a movement cue, or say "play steps 2 and 3", etc. The corresponding reference data structures 126 (e.g., cue[2], cue[3], etc.) are retrieved from the table of contents data structure 124 and de-referenced to identify the corresponding timestamps in video file 122 to replay. The video file 122 is displayed in the video player (e.g., video player 104 of FIG. 1A).

The exemplary instructional media data structure 120 integrates existing exercise video libraries and new instructional video libraries with minimal additional network overhead and/or storage impact. Notably, the table of contents data structure 124 can be created and annotated post-videography. Common examples of media technologies suitable for video files include without limitation e.g., MPEG (Motion Picture Experts Group), HEVC (High Efficiency Video Coding), and/or any other commonly used multimedia file type. Common examples of data structures useful for the table of contents data structure 124 include without limitation: timestamp markers, file handles, pointers, and/or other reference data structures.

Figure 1C:
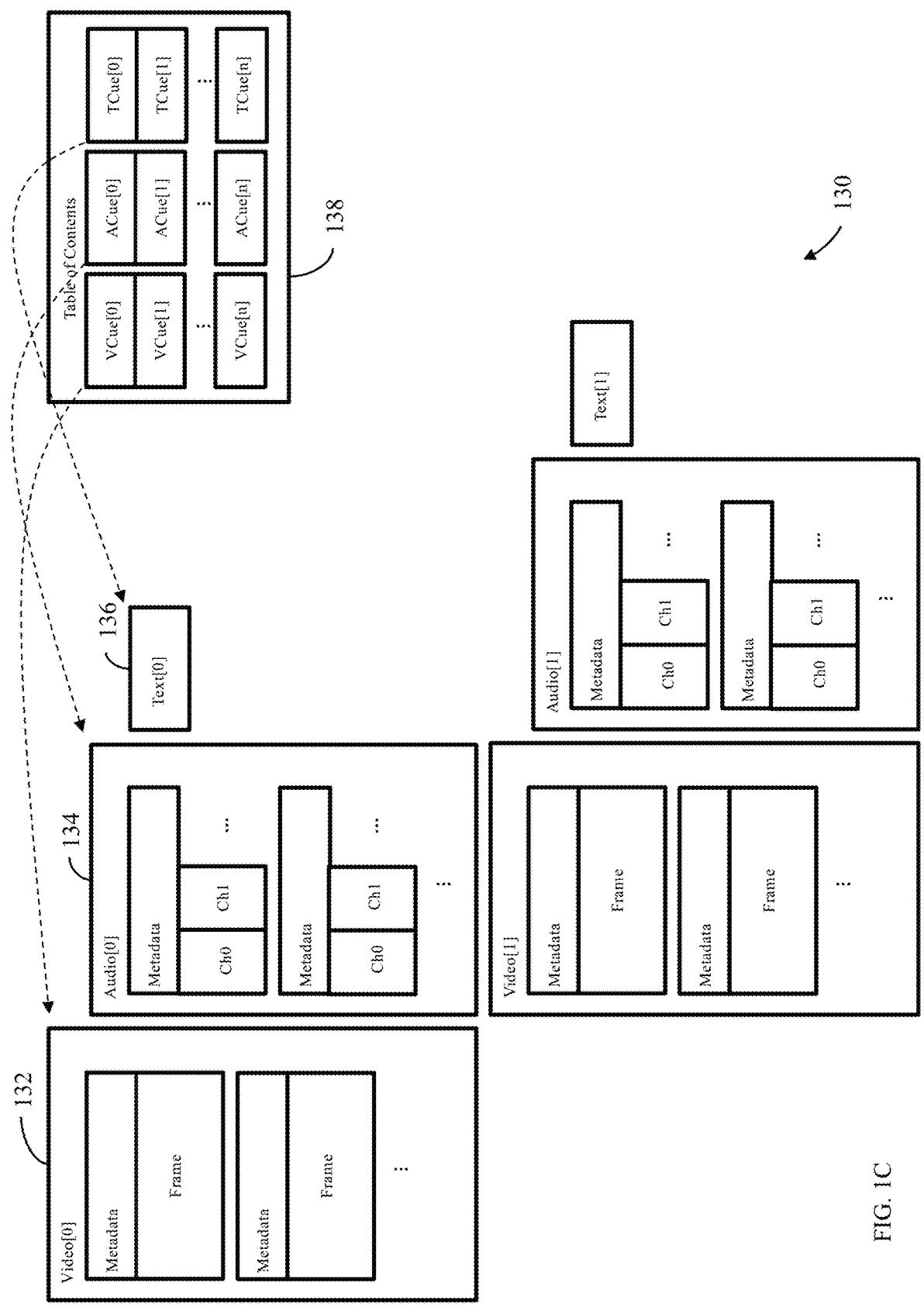

FIG. 1C is a graphical representation of another exemplary instructional media data structure 130. As shown in FIG. 1C, the instructional media data structure 130 includes video segments 132, audio snippets 134, text descriptions 136 and a table of contents data structure 138 with the corresponding reference data structures. Unlike the monolithic instructional media data structure 120 of FIG. 1B, instructional media data structure 130 has discrete component media that is organized according to the movement cue points associated with the exercise.

The corresponding reference data structures (e.g., vcue[1], acue[1], tcue[1], etc.) stored in the table of contents data structure 138 may be de-referenced to identify the corresponding video segments 132, audio snippets 134, and/or text descriptions 136 to retrieve and render. For instance, video segments 132 may be decoded in a video codec, audio snippets 134 may be played via an audio codec, and text descriptions 136 may be displayed in a separate breakout or overlaid on the video segment.

The exemplary instructional media data structure 130 enables selective construction, retrieval, delivery, and/or playback of hybrid media. In this manner, a client device may locally store subsets of the instructional media data structure that are tailored for the user's personal requirements. For example, a subset may include a text description of the entire exercise, and video segments and/or audio snippets for only a subset of the movement cues (the portions that a user is trying to focus their attention on). As previously alluded to, reducing a user's UI requirements (e.g., touch based navigation) while maximizing information density (movement specific instructional media) based on user-specific considerations provides heretofore unrealized benefits for fitness education.

Figure 1D:
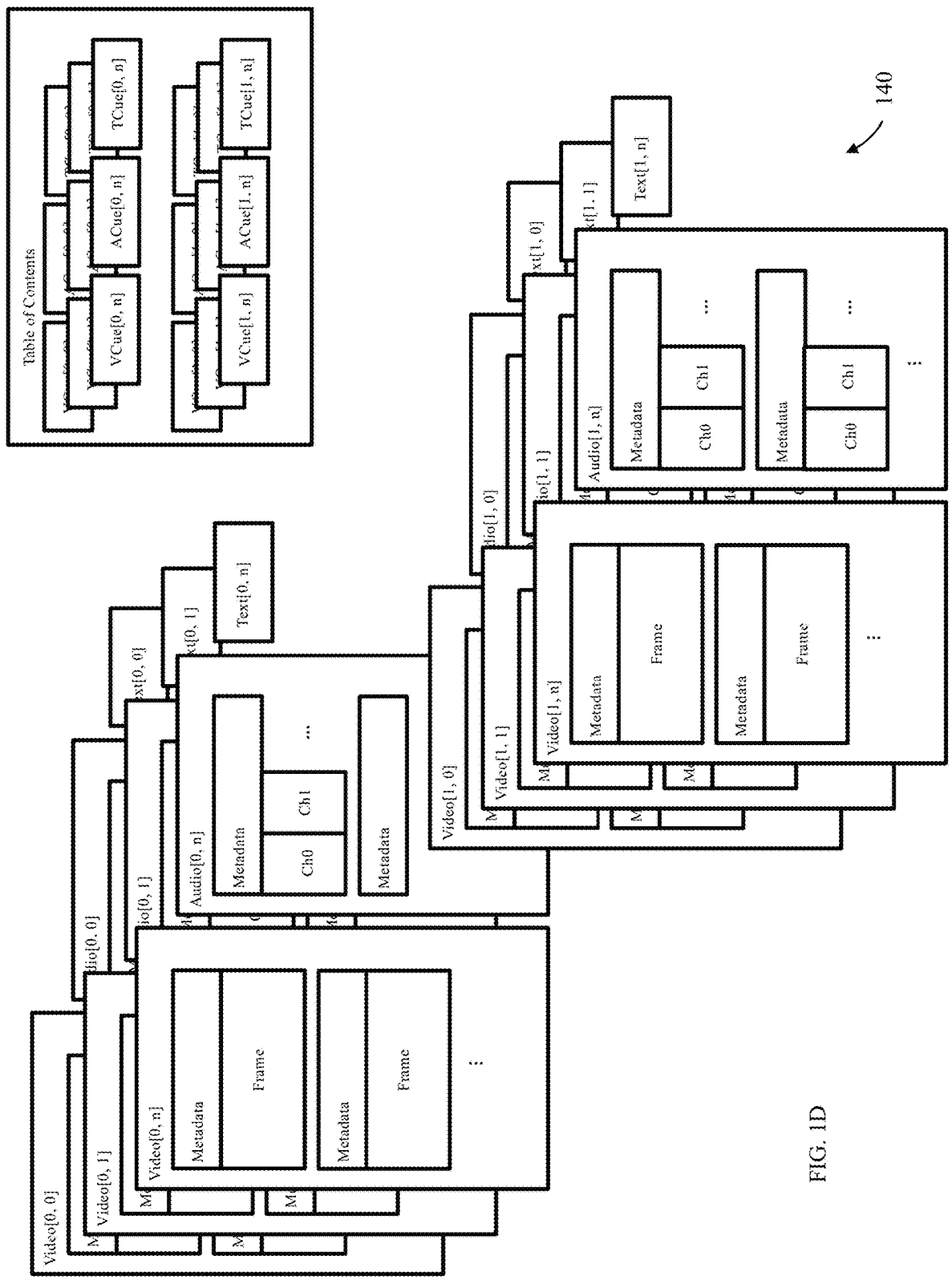

FIG. 1D is a graphical representation of yet another exemplary instructional media data structure 140. As shown in FIG. 1D, the instructional media data structure 140 includes multiple versions of video segments, audio snippets, text descriptions and a corresponding table of contents data structure with the corresponding reference data structures. The exemplary instructional media data structure 140 maximizes instructional media data structure configurability. As but one such example, a client device may locally store multiple exemplars of the same movement. This may be particularly useful to e.g., view the same movement cue from multiple different perspectives, on multiple different client devices (e.g., smart phone, smart watch, etc.), with multiple different models (e.g., age, gender, body types), etc.

The foregoing discussion of the exemplary implementation is purely illustrative; artisans of ordinary skill in the related arts may add, remove, and/or substitute similar functionality, given the contents of the present disclosure. More generally, various embodiments of the present disclosure ensure that users can focus their attention on learning the elements of proper form, even when they are mid-workout, so as to maximize workout efficacy and long-term outcomes.

Network Architecture

Figure 2:
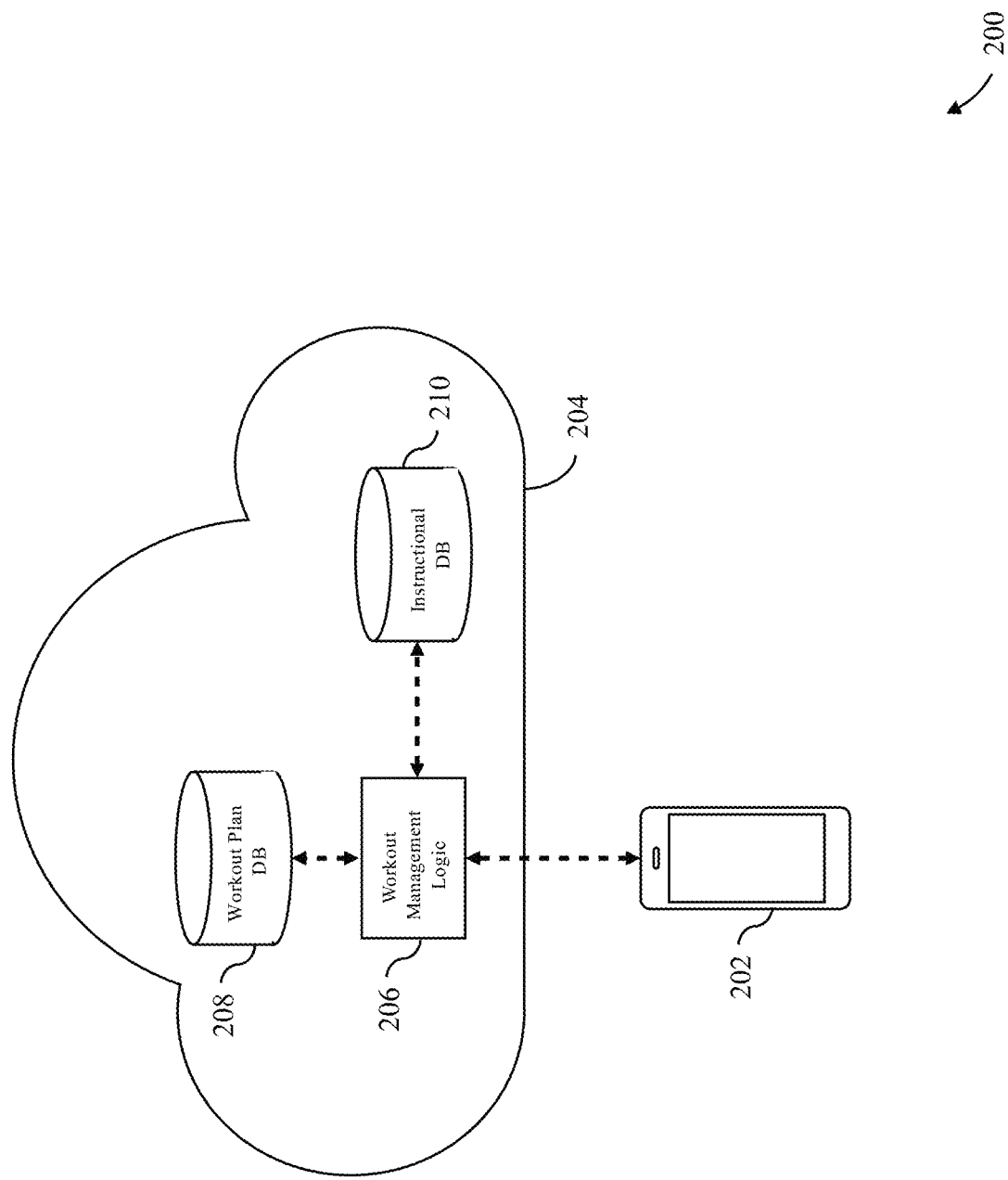
FIG. 2 is a logical block diagram of an exemplary network architecture configured to enable hybrid media playback according to cue points, in accordance with the various principles described herein.

Referring now to FIG. 2, an exemplary network architecture 200 configured to enable hybrid media playback according to cue points is shown. As illustrated, the network architecture 200 includes one or more user devices 202 in communication with a health and fitness network 204. In one exemplary embodiment, the health and fitness network 204 may include one or more of workout management logic 206 in communication with a user workout history database 208, and an instructional media database 210.

The health and fitness network 204 may include one or more wired and/or wireless, private and/or public network, including but not limited to, e.g., the Internet. The health and fitness network 204 is, for example, a wireless local area network (WLAN), wireless wide area network (WWAN), wired network, or any other suitable communication channel. Accordingly, each of the user devices 202, workout management logic 206, and databases (e.g., user workout history database 208, instructional video database 210) are configured with appropriate networking communication interfaces. An example of wired communication interface may include, but is not limited to, Ethernet; while examples of wireless communication interfaces may include, but are not limited to, near field communication (NFC), Bluetooth, Wi-Fi, 4G or 5G LTE. It is further appreciated that various gateways, routers, switches, base stations, and so forth may be involved in facilitating and forwarding communication between the foregoing devices. Additionally, it is noted that the foregoing health and fitness network 204 may be itself, composed of several networks, such that the described components are distributed in various ones thereof. In alternative embodiments, the health and fitness network 204 may include a series of devices communicating within software via software APIs (application programming interfaces).

As used herein, the term "database" refers to a structured set of data records held within a non-transitory computer-readable medium and/or the mechanisms used to e.g., add, remove, modify, and/or query and retrieve the stored data records. The term "data record" refers to a collection of data structures that represent an association, grouping, organization, or other collection of information; common examples of data structures include without limitation: numbers (integers, floating point), values (Booleans, enumerations), characters, strings, arrays (1D, 2D, N×D, etc.), lists, hash tables, etc. For example, a database may be queried for one or more data records that satisfy a particular condition; e.g., containing a particular string, value, etc.

The user workout history database 208 stores a plurality of user data records and their corresponding workout data records. Each user data record may include detailed information with regard to e.g., accuracy of data, fitness goal definition, progression of performance, psychological parameters (e.g., behaviors, motivations, etc.), height, weight, age, sex, ethnicity, and/or any number of other user specific parameters. Each workout data record may include detailed information with regard to e.g., date/time of past exercises, scheduled date/time of future exercises, type and/or number of exercises, frequency of exercise, exerted muscle groups, duration of exertion, intensity of exertion, absolute load, relative load, range of movement, repetition, recovery time, fatigue, dynamic feedback/user response, frequency of revision, revision success/failure, and/or any number of other workout specific parameters. More generally, artisans of ordinary skill in the related arts given the contents of the present disclosure, will readily appreciate that virtually any data regarding either the individual users and/or their specific workout history can be stored.

The instructional media database 210 stores a plurality of instructional media and reference data structures. In one embodiment, instructional media may include one or more constituent components. Common media component types may include, without limitation: video, audio, text, images, pictures, sounds, models (e.g., 3D wireframe, mathematical models etc.) and/or any other digital medium for rendering human comprehensible information. More generally, artisans of ordinary skill in the related arts will readily appreciate that any type of media may be substituted with equal success, the foregoing being purely illustrative.

As used herein, a "reference data structure" is a data structure that references another data structure (the referenced data structure). The reference data structure "refers" to data records within the referenced data structure; the data record can be accessed by "de-referencing" the reference data structure. In one such example, a timestamp may reference a particular frame within a video and/or an audio sample of an audio track. A codec can render the referenced frame/sample by de-referencing the timestamp and/or a frame associated with the timestamp. In another such example, a file handle (or pointer) may reference a particular video segment and/or an audio snippet. A codec can render the video segment and/or audio snippet by de-referencing the file handle (or pointer). Still other examples of reference data types include without limitation: handles, addresses, pointers, links, and/or any other form of associative data structure.

In one embodiment, workout management logic 206 may provide workouts to clients. For example, the user may have selected a workout plan to achieve a particular fitness goal. In other embodiments, workout management logic 206 may recommend workout plans to clients. For example, a user's workout data records may be analyzed for similarity to models of performance progression. For example, as described in co-owned, co-pending, U.S. patent application Ser. No. 16/588,199 filed Sep. 30, 2019 and entitled "METHODS AND APPARATUS FOR COACHING BASED ON WORKOUT HISTORY", incorporated herein by reference in its entirety, workout data for a population of different individuals may be analyzed to identify groups of similarly performing individuals. Each group of individuals may be analyzed to generate an expected profile that approximates the physiological and/or psychological traits of the group. A user's training plan can be initially selected and/or dynamically re-selected, based on their closest expected profile.

In one embodiment, workout management logic 206 further provides instructional media to users. As but one such example, a user's client device may be pushed instructional media data structures based on assigned exercises. In other examples a user's client device may pull instructional media data structures based on a user's input. Various other techniques for providing and/or obtaining data may be substituted by artisans of ordinary skill in the related arts, given the contents of the present disclosure.

In some embodiments, the instructional media data structures may include one or more constituent components retrieved from instructional media database 210. In some such cases, the instructional media data structure may be configured based on e.g., user configuration, network parameters, client device type, and/or other considerations. For example, the user may configure their client device to obtain video segments and text descriptions (and/or an associated table of contents data structure). In other examples, the client device may retrieve media types based on user interface considerations (e.g., a smart watch may only retrieve audio and/or text, etc.), processing or memory considerations (e.g., only a subset of video segments at a time), etc. Still other variants may be substituted by artisans of ordinary skill, given the contents of the present disclosure.

It is appreciated that in the illustrated embodiment, the aforementioned databases (208, 210) are separate and distinct from the workout management logic 206 and/or user device(s) 202. However, in other variants, the databases may be incorporated in part or in whole with either the workout management logic 206 and/or the user device(s) 202 for storage thereat. For example, instructional media may be cached locally at a particular user device 202 until e.g., viewed or replaced with other instructional media. Additionally, or in the alternative, instructional media (in whole or in part) may be stored at the workout management logic 206 and portions may be made accessible to particular devices 202 when queried and/or locally cached. Any combination of the foregoing configurations may be utilized with equal success.

While the foregoing example is presented in the context of strength training/calisthenic/cardiovascular type routines, artisans of ordinary skill in the related arts will readily appreciate that the various principles described herein may be readily adapted to virtually any activity e.g., sports activities, cooking, academic preparation, etc.

Methods

Figures 3A, 3B:
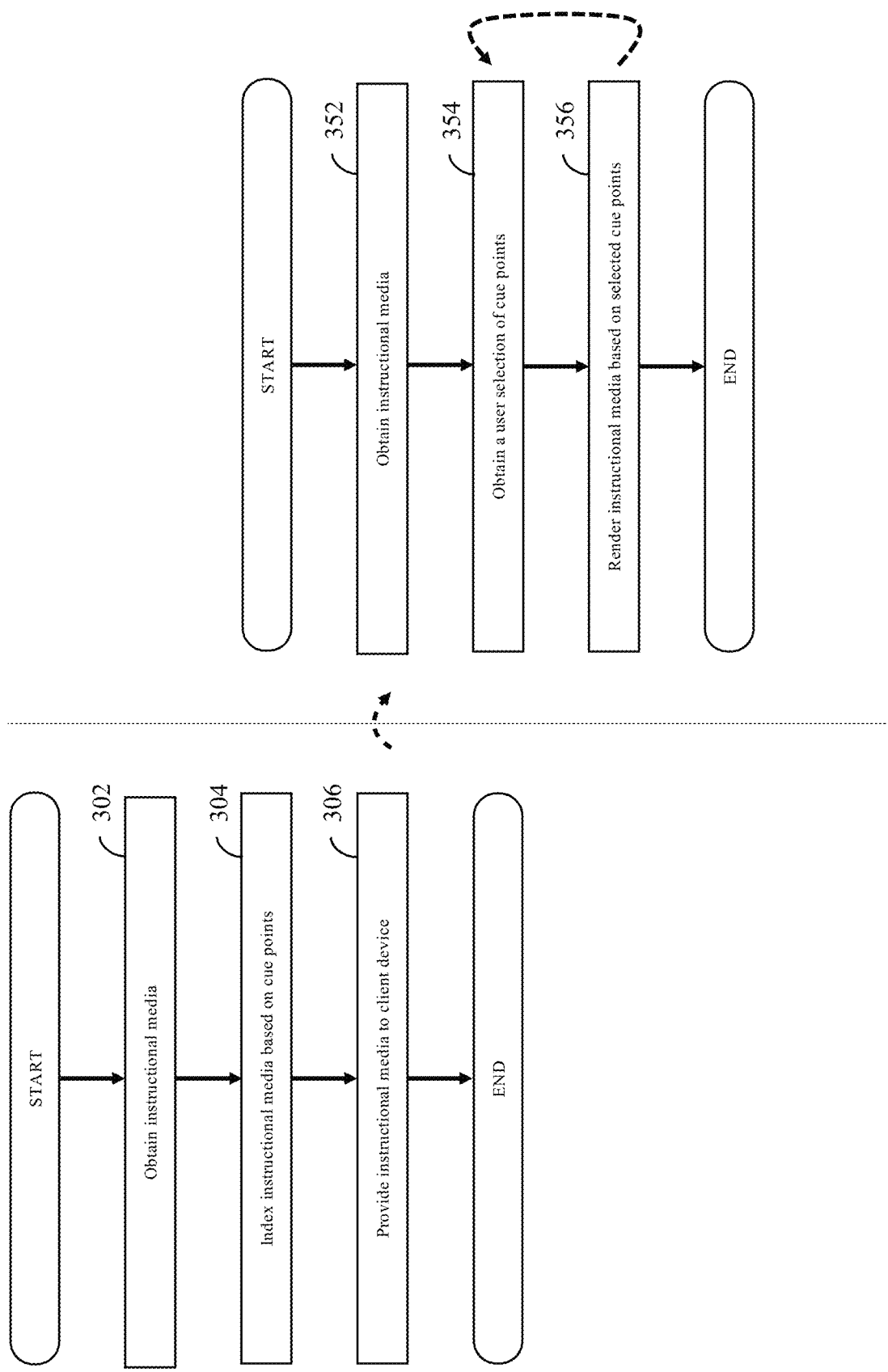
FIGS. 3A-3B are logical flow diagrams of exemplary methods for (i) providing instructional media based on cue points, and for (ii) hybrid media playback according to cue points, in accordance with the various principles described herein.

FIG. 3A is a logical flow diagram of an exemplary method 300 for providing instructional media based on cue points, in accordance with the various principles described herein.

At step 302 of the method 300, instructional media is obtained. In one exemplary embodiment, the instructional media describes an exercise. Other common examples of instructional media may include e.g., athletic activities, sports, cooking, professional skills, hobbies, academics, religious ceremonies, and/or any other activity. For example, a sport instructional may describe the various body movements both individually, and together as a fluid sequence. In another such example, a cooking instructional may describe the various steps for meal preparation (ingredients, cooking, and presentation). More generally, artisans of ordinary skill in the related arts given the contents of the present disclosure will readily appreciate that the principles described herein may be broadly applied to any instructional media.

As used herein, the term "media" refers to digital data that can be converted into perceptible form. Human perception includes sight, hearing, touch, taste, smell, balance and acceleration, temperature, proprioception, pain, etc. Common examples of media may include audio, video, text, and/or haptic media (touch based).

In some embodiments, instructional media may be paired with machine-readable tracks to enable dynamic machine interactions. For example, visual media describing body mechanics may be paired with machine-readable tracks for 3D motion capture apparatus to evaluate real-time performance. Similarly, audio media describing voice or music may be paired with machine-readable tracks for audio capture apparatus to determine e.g., vocal accuracy, tuning, etc.

As used herein, the term "instructional media" refers to media that instructs the intended audience to reproduce an action. As used herein, the term "cue" refers to measurable criteria for evaluating the action's reproduction. As used herein, the term "cue point" refers to a discrete identified point in the instructional media that is associated with a cue.

Instructional media may include a plurality of component media and/or cue points, which may be reproduced in sequence and/or concurrently. In exemplary implementations, each component is associated with a cue (e.g., a one-to-one mapping), however other implementations may use more complex mapping schemes. For example, a single video component may be used to demonstrate a swimming arm stroke in concert with a leg kick (e.g., one-to-many); alternatively, a single cue may have multiple video vantage points (many-to-one). Still other combinations may enable many-to-many mappings (e.g., multiple actions from multiple perspectives).

Instructional media may be obtained from a variety of sources. In one embodiment, instructional media is obtained via media capture techniques. For example, an exercise video instructional may be choreographed and captured by a team of professional videographers for a content hosting party (e.g., a $1^{st}$ party). In other embodiments, instructional media may be generated from $2^{nd}$ party trusted affiliates and/or $3^{rd}$ party amateur sources. Specifically, an external application programming interface (API) may be exposed to other parties to enable external media development for the content hosting party.

As but one such example, an exemplary API may enable a $2^{nd}/3^{rd}$ party to e.g., generate instructional media content, identify component media tracks, relevant cue points, and/or other relevant metadata. For instance, an amateur videographer may create an instructional video by uploading and identifying e.g., video segments, audio snippets, textual descriptions, and/or the corresponding table of contents data structure. Still other combinations will be readily appreciated by artisans of ordinary skill in the related arts.

In some cases, the $2^{nd}/3^{rd}$ party may also provide metadata that describes the instructional video; common examples of metadata may include without limitation: capture information (time, date, location), subject information (hashtags, search terms, categorization, model, author, contributors), audience information (e.g., target demographics, authentication and/or authorization requirements, etc.) Metadata is often helpful for database management, catalogues, filters, search engine optimization, and/or other data management techniques.

Common examples of $2^{nd}/3^{rd}$ party sources in the health and fitness industry include e.g., athletes, coaches, doctors, physical therapists, celebrities, and/or any number of other parties. For example, an athlete may be able to curate their own library of content and/or potentially monetize access to their library. In some such variants, the content hosting service may also monetize content delivery services and/or impose quality and/or quantity controls. As but one such case, a party may need to be "certified" as an expert in their area and/or be limited to a maximum number of uploads/downloads per time period. In still another such case, a party may be ranked (or promoted), thereby enabling the community of users to effectively navigate a large library of instructional media.

Another common example of $3^{rd}$ party content is so-called "crowdsourced" content. In a crowdsourced model, the user community may generate content for distribution to other users. Crowdsourcing has the potential to quickly generate large amounts of quality data at relatively low cost. In some cases, crowdsourcing may require privacy protections and/or security measures (e.g., Health Information Portability and Accountability Act (HIPAA) type protections). For example, certain types of instructional media may be user specific and/or user sensitive and thus require authorization and/or authentication safeguards. Examples of sensitive information within the health and fitness area may include without limitation e.g., physical ailment therapy, substance abuse treatment, etc.

In one such variant, different parties may collaborate together to provide different components of the instructional media. For example, a user may upload a video of their performance. A coach, personal fitness trainer, peer athlete, etc. may provide audio and/or textual annotations.

While the foregoing discussion is presented in the context of human generated content, artisans of ordinary skill in the related arts will readily appreciate that other methods for obtaining instructional media may be substituted with equal success. For example, instructional media may be computer generated based on models. As but one such example, movements may be choreographed by computer and illustrated with avatars (digital representations of people); e.g., avatars may be desired for a user's aesthetic preferences.

Similarly, while the foregoing discussion is presented in terms of instructional media; artisans of ordinary skill in the related arts will readily appreciate that there are broad applications within mechanical movement. For example, certain diagnostic endeavors may require humans to step through non-human movement cues (veterinary science, mechanical engineering, theatrical puppetry, etc.)

At step 304 of the method 300, the instructional media is indexed according to cue points. As used herein, the terms "index" and "indexing" refer to the process of generating a "reference data structure" to refer to data records within a data structure (the "referenced data structure"). Indexing may include creation and/or identification of physical and/or logical addresses and offsets in memory, enumerating namespaces, linking, and/or otherwise associating the reference data structure to the data records within the referenced data structure. Common examples of reference data types include without limitation: pointers, handles, arrays, linked lists, hash tables, namespaces, rendering identification (timestamp, row/column, etc.), data structure identification (e.g., frame number, channel number, etc.), and/or any number of other indirect addressing schemes.

In one exemplary embodiment, video data and/or audio data may be indexed according to timestamp, frame identifier (e.g., key frames), track numbers, track time, and/or any other temporal or spatial indicia. During operation, a codec may de-reference the cue point by e.g., identifying the appropriate frame to start rendering back the video segment. In another exemplary embodiment, video data and/or audio data may be indexed according to file handle, namespace, etc. During operation, a codec may de-reference the cue point by opening the appropriate file handle (or resolving a namespace identifier) to playback the identified file.

In some cases, instructional media may be segmented as part of the indexing process. As but one example, a human may watch the video and identify timestamps for cue points. Subsequently thereafter, the timestamps can be stored within a table of contents data structure for playback reference. In some cases, the timestamps may be used to physically segment the instructional media into different files. The video segment files are thereafter distinctly addressable and stored within a table of contents data structure based on file name (or other file handle). Additionally, artisans of ordinary skill in the related arts will readily appreciate that computer-assisted and/or computer alternatives may be substituted with equal success. For example, an artificial intelligence (AI) or machine learning (ML) algorithm may be trained to identify movement cue points based on e.g., image motion and/or commentary, pauses in motion and/or commentary, repeated sequences, etc. In some cases, AI/ML indexed content may be additionally verified (and refined) by a human expert.

Instructional media may be segmented, augmented, and/or translated during indexing. For example, an instructional video may be split into video components and audio components. Similarly, text overlays (such as via closed caption metadata) may be extracted for text descriptions. In other implementations, instructional media may be augmented with additional media. For example, a personal fitness instructor may provide tailored comments and/or motivational messages for their customers; e.g., "pay close attention to your knee positioning at this point", "you've really made strong progress in these areas, I just want you to keep it up", etc. As another example, a coach may add individualized feedback for his players which can be played alone (for individual review) or in-concert (for team review). Still other forms of indexing may enable translation; e.g., to support different language tracks (English, Spanish, French, etc.), to convert audio to text or vice versa, etc.

While the foregoing examples describe a "table of contents", virtually any reference data that maps cue points to their associated media components may be substituted with equal success. As previously alluded to, mappings between cue points and media components may be one-to-one, one-to-many, many-to-one, or many-to-many. For instance, the reference data structure may be an ordered list of media components (e.g., a linked list, array, etc.), an unordered collection (e.g., a relational database), graph structure (tree, hierarchical, cyclic graph, and/or acyclic graph), or combination thereof.

As but one such example, a movement cue for a squat ("walk up to the bar and grab it with your hands six inches wider than shoulder-width apart") may be subdivided into constituent sub-movement cues ("walk up to the bar", "grab it with your hands", "six inches wider than shoulder-width apart"), each of which may be further subdivided (e.g., "standard grip", "alternate grip", $3^{rd}$ party annotations, etc.) In other words, the instructional media may be subdivided into layers upon layers of detail. In this manner, both a breadth and depth of instruction media can be indexed and retrieved.

The foregoing illustrative discussions have been presented in the context of a single exercise, however the various principles described herein may be broadly applied to any instructional media of virtually any length, breadth, and/or depth of coverage. For example, a workout instructional media may group many exercises together, each of which may be individually segmented. For instance, a workout might include e.g., push-ups, pull-ups, squats, and sit-ups. The exercises may each be performed individually, or as part of the broader workout. The workout instructional media may actually be part of a larger training plan (which prescribes multiple workout types, etc.)

More generally, artisans of ordinary skill in the related arts will appreciate that the techniques described herein may enable a variety of flexible instruction media. For example, sports variants may cover multiple aspects of sports in whole, or piecemeal, e.g., a swimmer can learn arm strokes, leg kicks, etc. In cooking variants, multi-course meals may be composed of individual dishes, each of which is further broken down into component steps. In academic test preparation, the instructional may cover multiple subjects (logical reasoning, reading comprehension, and mathematics). Still other applications may be substituted by artisans of ordinary skill in the related arts, the foregoing being purely illustrative.

At step 306 of the method 300, the instructional media (or a portion thereof) is provided to a client device. In one exemplary embodiment, the instructional media may be "pulled" by a client device based on e.g., user interest, the user's profile, assigned workouts, or other client-side considerations. For example, a user may walk into their gym and identify equipment that is available (e.g., barbells, kettlebells, and seated row), responsively the health and fitness service can provide the user with instructional media based on what equipment is available, what the user might like to try, and/or what the user should exercise. In another such case, a set of instructional media may be pulled based on user input; for example, a user that has injured themselves may search for (and/or filter on) reduced impact workouts that minimally impact their injury. Similarly, a user that wants to vary their workout routine may look for new exercises to "spice up" their workouts.

In some cases, a super set of instructional media may be pushed to a user and cached for internal retrieval. As but one such example, a user may generally receive a suggested set of workouts that should be completed within e.g., a week. The health and fitness service may pre-load the user's client devices with corresponding instructional media. Thereafter, the user can learn about any of their exercises without requiring further network interaction. In another example, access to high demand equipment at a gym may be unpredictable. The user may pre-load exercise tutorials "just-in-case", so they can maximize short windows of opportunity.

In some situations, a combination of "push" and "pull" may be used. For instance, a user may pull a first set of instructional media and be pushed a second related set of instructional media. As but one example, a user may request pectoral exercises, which additionally cause related deltoid instructional media to be delivered in tandem. In another example, a user that has explicitly selected a generic set of exercise instructional may be pushed a targeted set of exercises more in line with their personal goals.

As previously alluded to, the instructional media may be included as part of a workout plan. In some cases, the workout plan may be selected by the user. For example, the user may browse from a selection of workout plans and select a workout plan of interest. In other cases, the workout plan may be recommended to a user based on e.g., the user's previous workout data and/or fitness goals. For example, as described in co-owned, co-pending, U.S. patent application Ser. No. 16/588,199 filed Sep. 30, 2019 and entitled "METHODS AND APPARATUS FOR COACHING BASED ON WORKOUT HISTORY", previously incorporated by reference in its entirety, workout data for a population of different individuals may be analyzed to identify groups of similarly performing individuals (e.g., profiles). A user's training plan can be initially selected and/or dynamically re-selected, based on their closest expected profile.

While the foregoing example is presented in the context of a health and fitness service and client device interaction, artisans of ordinary skill in the related arts will readily appreciate that instructional media may be provided via alternative sources and/or avenues. For example, a client device may send/receive media to/from other client devices and/or other parties; e.g., a smartphone that is paired to a smartwatch can provide media thereto. In other examples, a smartwatch may be able to cast the instructional media onto a larger screen (e.g., a nearby monitor or TV). Similarly, a user may be able to instructional media to a training partner, etc. In some cases, user transfers may occur in a unicast, broadcast, and/or multicast manner; for example, a coach may send a team different sets of instructional media. Each athlete may have their own set of component media, in addition to the team-wide media.

The devices described herein are not limited to the user's own devices and/or a health and fitness service. Smart communal gym equipment may greatly facilitate user experience e.g., a smart shoulder press may directly communicate with a user's smart phone to provide instructional media without external network connectivity. In a similar case, smart gym equipment may include workout UIs that can retrieve pre-loaded instructional media from the user's device. Still other variants of the foregoing may be readily substituted by artisans of ordinary skill, given the contents of the present disclosure.

FIG. 3B is a logical flow diagram of an exemplary method 350 for hybrid media playback according to cue points, in accordance with the various principles described herein.

At step 352 of the method 350, instructional media is obtained. As previously noted, the instructional media may be pushed to and/or pulled by the client device from a variety of sources. For instance, the instructional media may be received from a content service (e.g., a health and fitness network), a peer device (e.g., a workout partner's device, smart gym equipment, etc.), etc. In some embodiments, the client device may perform authorization, authentication, and/or certification checks. As but one such example, an athlete may only accept instructional media from their coach, teammates, or other known sources. In other examples, a user that has joined a new gym may be open to trying new exercises; however, they may require that the instructional media has a minimum certification or other equivalent reputation.

In some embodiments, the client device may locally trim and/or add to instructional media. For example, a workout plan may come with instructional media for all of the exercises. The client device may automatically trim the instructional media to just the portions which the user is currently prescribed to do. In another example, two users may exchange instructional media via a peer-to-peer exchange; each user has only a subset of the instructional media because they were focused on different cues. Post-transfer, the client devices may retrieve missing media components and/or purge unnecessary media components from e.g., a health and fitness network.

In some embodiments, the client device may locally augment instructional media. In one such variant, a primary instructional media may be provided via a health and fitness network, however the instructional media may incorporate $3^{rd}$ party annotations via e.g., affiliated networks. For example, a cue may be associated with a video segment, a textual description, and an XML link to a $3^{rd}$ party audio content server that stores $3^{rd}$ party audio annotations (personal fitness trainers, coaches, teammates, etc.) In another such variant, the user may have private annotations that can be locally augmented directly at the client device.

In some embodiments, the client device may additionally push the instructional media to a nearby device. For example, a user that receives instructional media at their smart phone may also push some portions of the instructional to e.g., a smart watch, or nearby smart gym equipment. In other embodiments, the client device may push the instructional media to a nearby peer device; for example, certain types of applications (e.g., cooking) can be performed in teams, different people can handle different steps of meal preparation.

At step 354 of the method 350, the client device obtains user selection of cue points for playback. In one exemplary embodiment, the user interface (UI) is optimized for discrete cue point media playback and/or manipulation. Typical examples of user selectable cue point playback navigation may include e.g., starting cue point, ending cue point, cue points to skip, cue points to include, and/or media selection (e.g., video vantage point, video with audio, video only, audio only, etc.)

In one exemplary embodiment, the client device may automatically display a textual overview of the cues to enable a user to select various ones of the cue points for video and/or audio playback. In other implementations, the instructional media may "auto-play" by default but enable the user to switch into cue point navigation.

While the foregoing examples are presented in the context of a sequential ordering, more sophisticated embodiments may allow the user to identify a playback sequence. For example, concurrent actions (e.g., a swimming arm stroke in concert with a leg kick) may be played in any order. Similarly, multiple vantage points of the same action may be swapped (e.g., top view then side view, or side view then top view, etc.) Still other applications may benefit from non-sequential skip ahead capabilities. As but one example, cooking applications often assume a single cook and sequence meal preparation sequentially; however, when multiple cooks are simultaneously working, preparation steps can be pipelined (e.g., one cook can work on one task, while another cook does another task in parallel).

As previously alluded to, the aforementioned illustrative user interfaces (UIs) are optimized for discrete cue point media playback within the context of a fitness application (e.g., a gym, or other athletic activity). Specifically, most client device user interface (UI) components fail to accurately register touch location in common workout scenarios, furthermore generic "slider" interfaces do not identify salient locations in the media. Consequently, the exemplary embodiments of the present disclosure enable cue point navigation based on robust and/or error-tolerant interface elements e.g., on-off type components (e.g., checkboxes, radio buttons, etc.), large "hit boxes" (where a touch anywhere within the hit box qualifies as a "hit"), gesture-based interactions (swipe left, right, up, down), multi-finger gestures (pinch to zoom in/out, multi-finger rotate, etc.), tap patterns (e.g., double-tap, multi-finger tap, or some hybrid thereof), voice instruction, motion control, etc. In one exemplary embodiment, text descriptions of a movement cue can be provided in hit boxes; a user selection anywhere within the hit box results in a user selection of the cue point.

More generally, artisans of ordinary skill in the related arts given the contents of the present disclosure will appreciate that certain applications do not match the traditional assumptions regarding user interface (UI) and/or usage. Common examples of such assumptions may include e.g., visibility (brightness, color, contrast, etc.), audibility (volume, clarity, etc.), input accuracy, environment (e.g., humidity, temperature, interference, etc.) While the foregoing disclosure is presented in the context of fitness applications (e.g., gym environments), other environments may have different usages and/or require different modifications. For example, in a cooking context, grease and fat may not only interfere with device accuracy but may further be difficult to clean from the device afterwards. Thus, voice control may be more desirable (e.g., "what's the next step in the recipe", "go back to the previous step", etc.) As but another example, sterile applications (e.g., medical applications, etc.) may use disposable components that can be thrown away after procedures; for example, a device screen may provide visual media and text, but accept inputs from a disposable keypad (one-time, single patient use). Still other substitutions may be made by artisans of ordinary skill, in view of the foregoing discussions.

Referring back to step 354 of the method 350, certain embodiments may enable media manipulation via the optimized cue point navigation. As a brief aside, existing media players use a monolithic data structure for media playback, for example, video frames, text overlays, and/or audio tracks are incorporated within a common data structure (see e.g., MPEG and/or HEVC formats). Notably, the monolithic data structure assumes that the encoding system (e.g., a content delivery network (CDN)) can encode the content once, for a myriad of different decoding devices of various capability (e.g., from large televisions and PCs to smart phones and portable media players, etc.) The foregoing assumption is ill-suited for applications where the decoding device may dynamically modify the content for playback. Conceptually, while artistic content is often meant to be viewed in a particular way, educational content is most effective when it focuses on what the viewer should learn (which is different for every viewer).

Within the context of the present disclosure, user selections may dynamically affect which media should be played. In this manner, a user can absorb the instructional media content in the manner that is most effective for the user's specific problems. As but one such example, a user can dynamically select which media components to play. For example, the user may dynamically skip to only the portions of the instructional media that show muscle groups of interest. In other scenarios, an athlete may e.g., select to play the default media, but replace generic video/audio/text with their coach's annotations.

Still other variants may enable personalization of instructional media either in whole, or in part. For instance, a user may obtain personalized media components (e.g., the video segments may use a model of similar gender, age, height, weight, musculature, ethnicity, accessibility, etc.) Still other user selections may be based on e.g., alternate styles/forms (e.g., to change muscle group focus, change flexibility requirements, compensate for injury or limited mobility, etc.), locale (language over), chirality (left-handed or right-handed), etc.

While the foregoing discussion is presented in the context of traditional audio and/or visual media, artisans of ordinary skill in the related arts will readily appreciate that the various principles described herein can be used to hybridize instructional media components with new forms of media. In one such embodiment, an existing video segment may incorporate $3^{rd}$ party annotations. As but one such example, drawings, sketches, and/or other human created overlays can be added as a novel media type. For example, the annotation may be a drawing with a transparent background (e.g., commonly used in portable network graphic (PNG) type images). In this manner a coach may provide athlete's with overlays that emphasize proper form.

In yet another such example, an athlete may capture videos of their own exercise, and annotate their corresponding cue points. The client device can thereafter render both athlete's video with a model video (e.g., a "capture-and-compare"). Notably, in some cases, the client device may speed up and/or slow down either videos based on cue points. In this manner, the athlete can see an apples-to-apples comparison; this may be particularly useful for fluid movements, where timing is hard to quantify. In some such variants, the aforementioned overlay annotations may be combined with the capture-and-compare capabilities, so as to give even clearer illustrations. As but one such example, an overlay showing e.g., posture of the model could be presented with an overlay for the athlete's posture. Still other variants may incorporate e.g., wire frame models, stick figure representations, etc.

Referring back to step 354 of the method 350, the client device may consider other client-side considerations in addition to user input. In one such variant, client device may be configured to select certain types of media based on user attention. For example, the device may play video only when the user is looking at the device (e.g., as determined by facial recognition, detection, etc.); otherwise, the device plays audio only. Still other variants may search for nearby devices (e.g., smart watches, smart gym equipment, etc.) to render instructional media; for example, a client device may cast the instructional media to a smart gym equipment (or vice versa). Still other variants may detect environmental conditions (e.g., time, location, ambient noise, etc.) e.g., a user that selects instructional media in a noisy gym may be better served by text overlays than audio, etc.

At step 356 of the method 350, the client device renders the instructional media based on the user selection of cue points. In one exemplary embodiment, the instructional media combines multiple different media components in a hybrid media playback.

Playback navigation may include a variety of different capabilities. Common examples of playback navigation may include e.g., play, pause, stop, start over, skip to next media, fast forward, reverse, skip ahead (by time increment or cue point), skip back (by time increment or cue point), etc. Other common playback options may include without limitation, play and stop, "boomerang" (play forward and reverse play), loop play, play in sequence (playlist), playlist repeat, and/or any other variation thereof. Additionally, playback options may include support for e.g., different speeds (e.g., 4×, 2×, 1×, ½×, ¼×, etc.), zoom in, zoom out, etc.

In some implementations, the client device may be able to render multiple media components in parallel. For example, a video display may offer both a primary video and a secondary video; common examples of such displays include e.g., window players and/or picture-in-picture (PIP). In one such variant, the user may identify which media components should be played in the primary player and which should play in the second player; this may be particularly helpful for complicated motions. For instance, a swimming instructional may provide e.g., arm stroke, and leg kicks in the primary player, while simultaneously illustrating the entire motion in concert in the secondary player (or vice versa). In still another example, a cooking instructional may show both the current meal preparation stage, while simultaneously showing a parallel process in a PIP (e.g., a sauce reduction, simmer, etc.)

In some embodiments, the client device may operate multiple codec chains in parallel. For example, video segments may be handled by a video codec, whereas audio snippets may be handled by an audio codec. More directly, artisans of ordinary skill in the related arts will readily appreciate that the division of instructional media components into separate data structures may be substantially improved by parallelized hardware decoding (e.g., rather than context switching between different media files in a shared codec). Still other hardware optimizations for handling the foregoing data structures may be readily appreciated by artisans of ordinary skill, given the contents of the present disclosure.

Apparatus

Figure 4A:
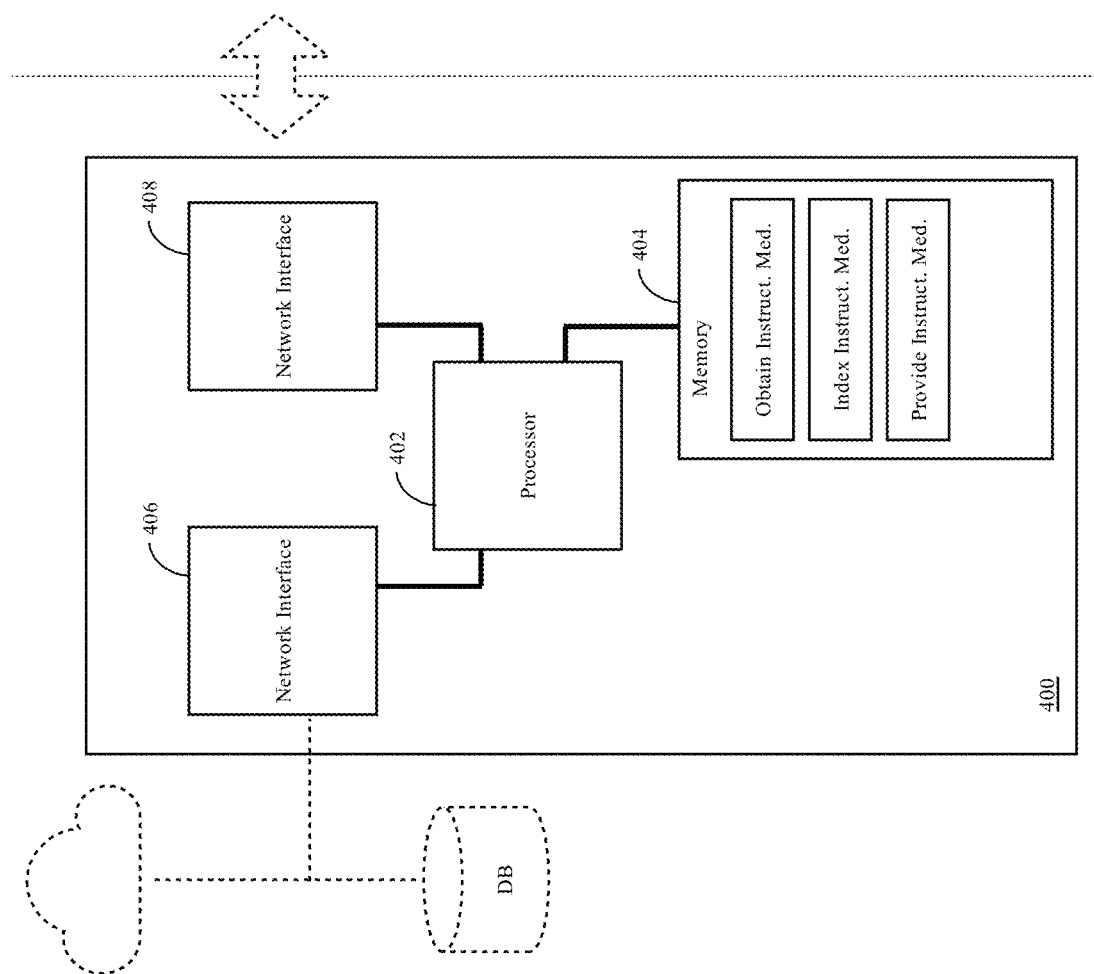
FIGS. 4A-4B are logical block diagrams of exemplary server apparatus, and client device, in accordance with the various principles described herein.

FIG. 4A is a logical block diagram of one exemplary server apparatus 400, useful in accordance with the various principles described herein. In one embodiment, the server apparatus 400 includes a processor 402, non-transitory computer-readable medium 404, and one or more network interfaces (e.g., a first network interface 406, and a second network interface 408).

The components of the exemplary server apparatus 400 are typically provided in a housing, cabinet or the like that is configured in a common manner for a server or related computing device. It is appreciated that the embodiment of the server 400 shown in FIG. 4A is only one exemplary embodiment of a server 400 for the health and fitness system. As such, the exemplary embodiment of the server 400 described herein with reference to FIG. 4A is merely representative of any of various manners or configurations of servers or other data processing systems that are operative in the manner set forth herein.

The processing circuitry/logic 402 of the server 400 is operative, configured, and/or adapted to operate the server 400 including the features, functionality, characteristics and/or the like as described herein. To this end, the processing circuit 402 is operably connected to all of the elements of the server 400 described below.

The processing circuitry/logic 402 of the host server is typically controlled by the program instructions contained within the memory 404. The program instructions 404 are configured to provide instructional media based on cue points to client devices, as described in further detail supra. The health and fitness program at the server 400 may be configured to communicate with and exchange data with a client-side application running on a processor of a personal device. In addition to storing the instructions, the memory 404 may also store data for use by the health and fitness program. As previously described, the data may include the workout data records, personal data records, and instructional media, etc.

The network interfaces of the server 400 allow for communication with various devices using various means. In one particular embodiment, the network interface is bifurcated into a first network interface 406 for communicating with other server apparatuses and a second network interface 408 for communicating with a client device. Other implementations may combine these functionalities into a single network interface, the foregoing being purely illustrative.

In one exemplary embodiment, the first network interface 406 is a wide area network port that allows for communications with remote computers over the Internet (e.g., external databases). The first network interface 406 may further include a local area network port that enables communication with any of various local computers housed in the same or nearby facility. In at least one embodiment, the local area network port is equipped with a Wi-Fi transceiver or other wireless communications device. Accordingly, it will be appreciated that communications with the server 400 may occur via wired communications or via the wireless communications. Communications may be accomplished using any of various known communications protocols.

In one exemplary embodiment, the second network interface 408 is a network port that allows for communications with a community of personal devices. The second network interface 408 may be configured to interface to a variety of different networking technologies consistent with consumer electronics. For example, the network port may communicate with a Wi-Fi network, cellular network, and/or Bluetooth devices.

In one exemplary embodiment, the server 400 is specifically configured to provide instructional media based on cue points in accordance with the principles described above. In particular, the illustrated server apparatus 400 stores one or more computer-readable instructions that when executed e.g., obtains instructional media; indexes the instructional media according to the cue points; and provides the instructional media (in whole or part) to a client device.

Figure 4B:
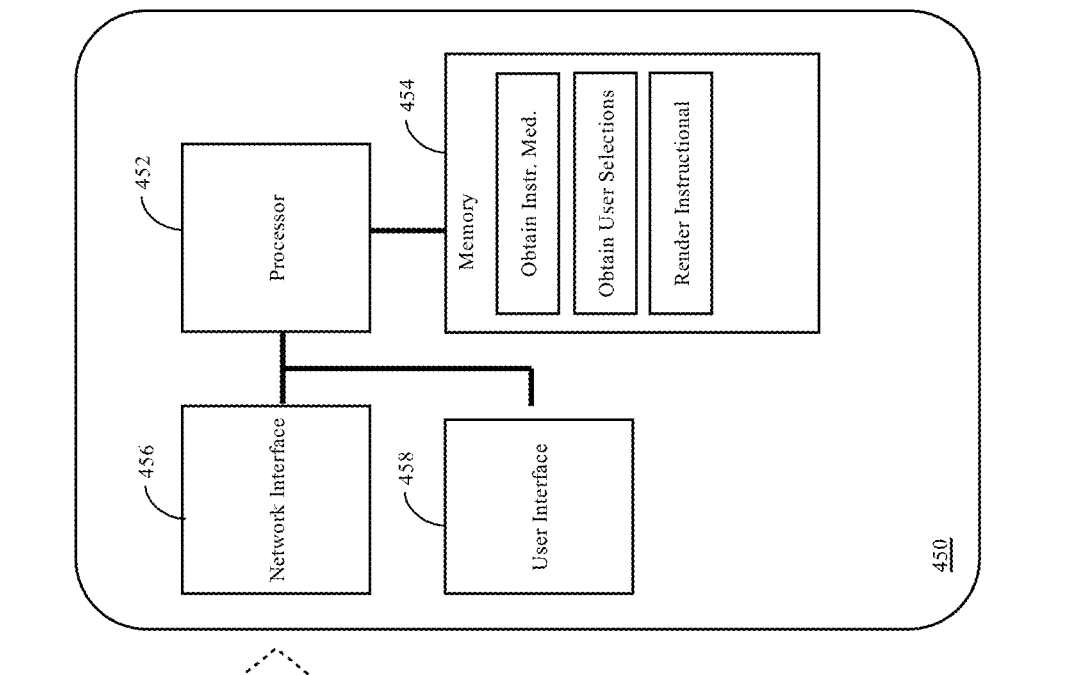

FIG. 4B is a logical block diagram of one exemplary client device 450, useful in accordance with the various principles described herein. In one embodiment, the client device 450 includes a processor 452, non-transitory computer-readable medium 454, a first network interface 456, a user interface 458.

The components of the exemplary client device 450 are typically provided in a consumer electronics personal device such as a laptop, smart phone, etc. In some cases, the components of the exemplary client device 450 may be provided in a wearable form factor that is configured for everyday use and/or ruggedization. Examples of wearables include e.g., smart watches, smart shoes, pedometers, headphones, smart clothing, smart jewelry, smart glasses (and other head mounted displays), implantable devices, etc. It is appreciated that the embodiment of the client device 450 shown in FIG. 4B is only one exemplary embodiment of a client device 450 for the health and fitness system. As such, the exemplary embodiment of the client device 450 described herein with reference to FIG. 4B is merely representative of any of various manners or configurations of personal devices that are operative in the manner set forth herein.

The processing circuitry/logic 452 of the client device 450 is operative, configured, and/or adapted to operate the client device 450 including the features, functionality, characteristics and/or the like as described herein. To this end, the processing circuit 612 is operably connected to all of the elements of the client device 450 described below.

The processing circuitry/logic 452 of the client device 450 is typically controlled by the program instructions contained within the memory 454. The program instructions 454 enable hybrid media playback according to cue points, as described in further detail supra. The client-side application at the client device 450 is configured to communicate with and exchange data with a host-side application at the health and fitness system as well as any number of other personal devices. In addition to storing the instructions, the memory 454 may also store data for use by the client-side application. As previously described, the data may include the workout data records, personal data records, and/or instructional media, etc.

In one exemplary embodiment, the client device 450 is specifically configured to playback hybrid media according to cue points in accordance with the principles described above. In particular, the illustrated client device 450 stores one or more computer-readable instructions that when executed e.g., obtains instructional media; obtains user selection of cue points for playback; and renders the instructional media based on the user selection of cue points.

The network interfaces of the client device 450 allow for communication with various devices using various means. In one particular embodiment, the first network interface 456 enables communications with the health and fitness system and/or nearby peer devices. Other implementations may combine these functionalities into a single network interface, the foregoing being purely illustrative.

In one exemplary embodiment, the first network interface 456 is a local area network port that allows for communications with computers over an Ethernet connection (e.g., the health and fitness server 400). In another embodiment, the first network interface 456 is a cellular network port that allows for communications with a base station (that operates as a gateway to the broader Internet). In still other embodiments, the first network interface 456 may be configured to interface to a variety of different networking technologies consistent with consumer electronics. For example, the network port may communicate with a Wi-Fi network, cellular network, and/or Bluetooth devices. Communications may be accomplished using any of various known communications protocols.

In one exemplary embodiment, the user interface 458 is the interface that allows for communication between the user and the device. Common examples of human-machine input devices include elements such as e.g., touch screens, microphones, speakers, keypads, mice, buttons, and/or any number of other human input devices. In some variants, the user interface 458 may allow for unobtrusive communication between the user and the device via e.g., tactile, haptic, auditory, and/or time-insensitive visual interfaces. Common examples of such human-machine input devices include elements such as e.g., touch screens, microphones, speakers, buttons, rumble boxes, vibrators, and/or any number of other human input devices.

As used herein, the term "workout" refers to one or more activities performed by the user with measurable physiological and/or psychological impact. Examples of measurable physiological impacts may include without limitation e.g., cardiovascular strain, heart rate, caloric consumption, muscular exertion, fatigue, blood oxygenation, lactate production, blood occlusion, nervous system activation, temperature increase, sweat production, changes to form/body positioning (via video analysis), audible data (exhalations, foot strikes, etc.), and/or any other physical effect of exertion. Physiological data may be collected via one or more sensors and/or the user device interface (e.g., buttons, touch screen, microphones, etc.). Common examples of sensors include e.g., accelerometers, heart rate monitors, blood sensors, microphones, cameras, etc.

As used herein, "performance" and "performance metrics" refer to any set of workouts and/or predicted/expected physiological and/or psychological impacts for similar users based on e.g., physiology, psychology, fitness goals and/or any other relevant parameters. As used herein, the term "performance progression" is used to refer to a user's tolerable physiological and/or psychological impact as a function of time. For example, a user's physiological progression may be measured as a function of e.g., changes to heart rate as a function of distance run over multiple workouts, changes to maximum repetitions/sets of a load over multiple workouts, etc. Notably, while performance progression is generally measured physiologically, psychological measures may also have significant value. For example, some users may subjectively enjoy working out regardless of whether or not they improve their physiological performance. Also, a user's psychological impact may cause changes to motivation and/or outlook when they hit a physiological "plateau."

The above described system and method solves a technological problem common in industry practice related to navigating instructional media during playback in common fitness environments. The above-described system and method improves the functioning of the computer/device by enabling users to focus on specific portions of interest using cue point navigation.

Portions of the system and methods described herein may be implemented using one or more programs or suitable software code, such as the workout application on the client device and the health and fitness program on the server, both described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer-readable medium can be, by way of example, only but not by limitation, an electronic, magnetic, optical, electromagnetic, infrared, or semiconductor system, apparatus, system, device, or computer memory. The computer-readable medium may include multiple computer-readable media storing computer executable instructions, such as in a distributed system or instructions stored across an array. A "non-transient computer-readable medium" may be any type of data storage medium that can store computer instructions, including, but not limited to the memory devices discussed above.

In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

Figure 5:
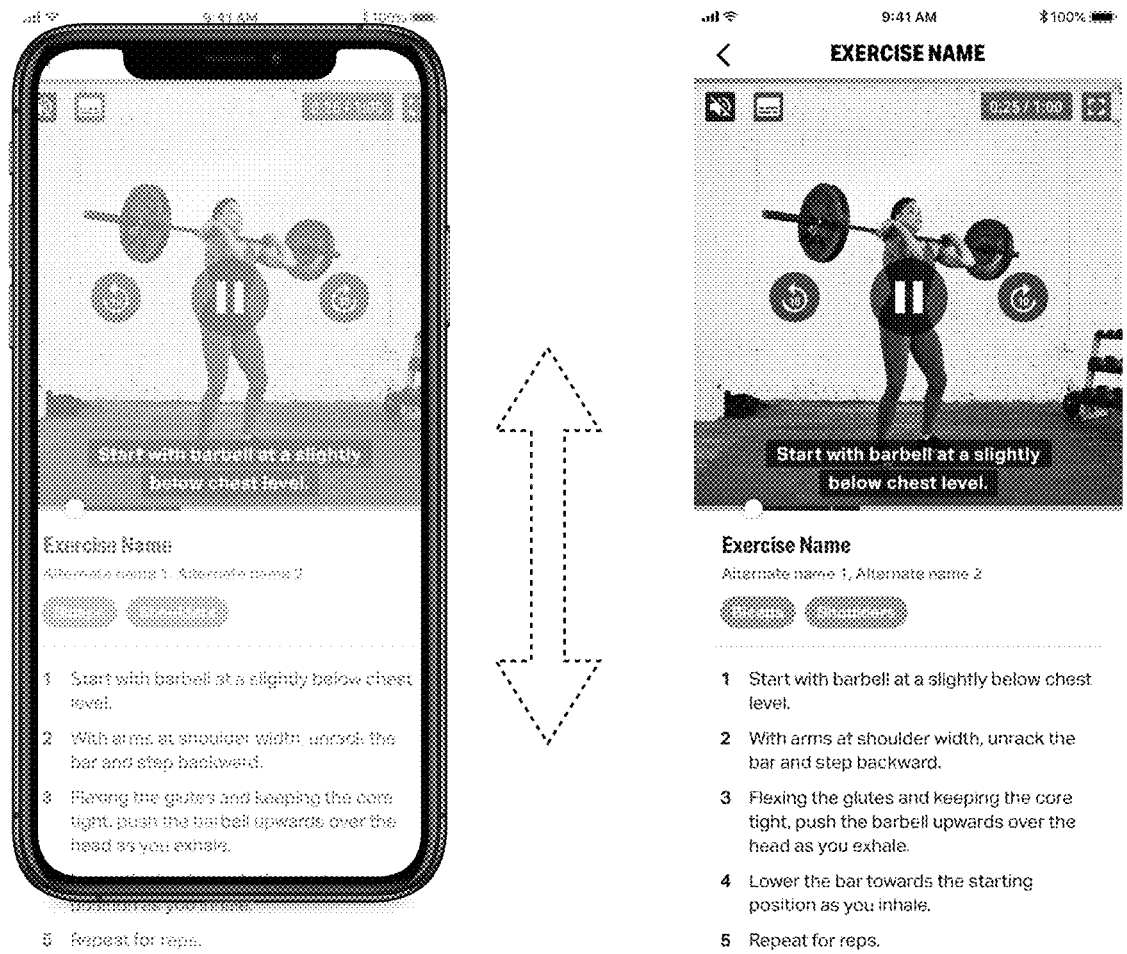
FIG. 5 is a graphical representation of an exemplary user interface, consistent with the various principles described herein.

FIG. 5 depicts graphical representations of an exemplary user interface, consistent with the various principles described herein.

FIG. 5 illustrates a user interface for hybrid media playback based on movement cue points. The cue point navigation focuses user attention on specific portions of interest using cue point navigation. Additionally, the reduced complexity user interface is optimized for workout environments.

The foregoing detailed description of one or more exemplary embodiments of the health and fitness system with instructional media and hybrid media playback has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

In another embodiment, a permanent copy of the programming instructions for individual ones of the aforementioned applications may be placed into permanent storage devices (such as e.g., memory) during manufacture thereof, or in the field, through e.g., a distribution medium (not shown), such as a compact disc (CD), or through communication interface (from a distribution server). That is, one or more distribution media having an implementation of the agent program may be employed to distribute the agent and program various computing devices.

It will be appreciated that the various ones of the foregoing aspects of the present disclosure, or any parts or functions thereof, may be implemented using hardware, software, firmware, tangible, and non-transitory computer-readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A user apparatus, comprising:
a user interface;
a network interface;
a processor; and
a non-transitory computer-readable medium comprising one or more instructions, which when executed by the processor, causes the user apparatus to:
obtain instructional media for a cooking instruction describing a plurality of steps for a meal preparation, where the instructional media comprises a plurality of cue points associated with a plurality of media components of the instructional media, the plurality of media components including a plurality of video segments, each of the plurality of cue points associated with (i) a video segment associated with one of the steps of the cooking instruction, and (ii) a different timestamp within the instructional media for the cooking instruction;
obtain a first user selection of a first cue point associated with a first timestamp within the instructional media and a start of a first step of the plurality of steps of the cooking instruction;
render a first video segment of the instructional media, wherein the first video segment is associated with the first cue point;
obtain a second user selection of a second cue point different from the first cue point, where the second cue point is associated with a second timestamp within the instructional media, a start of a second step of the plurality of steps of the cooking instruction, and a second video segment of the instructional media, wherein the second timestamp is different from the first timestamp; and
render the first video segment associated with the first step of the cooking instruction and the second video segment associated with the second step of the cooking instruction concurrently on the user interface such that the first step of the cooking instruction and the second step of the cooking instruction are shown simultaneously on the user interface, the first video segment and the second video segment rendered from the first cue point and the second cue point, respectively.

2. The user apparatus of claim 1, the one or more instructions when executed by the processor further causes the user apparatus to:
  display a plurality of text descriptions associated with the plurality of cue points;
  wherein the user selection of the first cue point comprises a hit within a hit box of a first text description.

3. The user apparatus of claim 1, wherein the plurality of video segments are comprised of a plurality of video frames.

4. The user apparatus of claim 1, wherein the plurality of media components include video files and the plurality of cue points are file handles.

5. The user apparatus of claim 1, the one or more instructions when executed by the processor further causes the user apparatus to:
  obtain a third user selection of a third cue point; where a third media component is associated with the third cue point; and render the first media component and the third media component in sequence.

6. The user apparatus of claim 1, further comprising a hardware codec; wherein the first video segment is rendered via the hardware codec, and the second video segment is rendered via a software process.

7. The user apparatus of claim 1 wherein the plurality of steps for meal preparation includes two or more of ingredient collection, cooking, and meal presentation.

8. The user apparatus of claim 1 wherein the plurality of steps for meal preparation include a plurality of parallel processes of the cooking instruction that may be performed concurrently, and wherein the first media component and the second media component are parallel processes of the cooking instruction.

9. The user apparatus of claim 1 wherein the plurality of steps for meal preparation includes preparation of a multi-course meal comprised of a plurality of individual dishes, wherein preparation of each individual dish of said multi-course meal is further broken down into component steps.

10. A method for rendering hybrid media based on cue point navigation, the method comprising:
  displaying a plurality of text descriptions of a plurality of sequential steps of a cooking instruction via a touch screen interface;
  responsive to a first user selection of at least one text description:
    retrieving a reference data structure from a table of contents data structure;
    de-referencing the reference data structure to identify a first video segment in an instructional media data structure, the first video segment associated with a first sequential step of the cooking instruction; and
    playing the first video segment via the touch screen interface; and
  responsive to a second user selection of a second text description:
    retrieving a second reference data structure from the table of contents data structure;
    de-referencing the second reference data structure to identify a second video segment in the instructional media data structure, the second video segment associated with a second sequential step of the cooking instruction that is after the first sequential step of the cooking instruction; and
    playing the first video segment and the second video segment concurrently via the touch screen interface such that the first step of the cooking instruction and the second step of the cooking instruction are shown simultaneously on the user interface.

11. The method of claim 10, wherein de-referencing the reference data structure to identify the video segment in the instructional media data structure is further based on one or more user personalization data.

12. The method of claim 10, further comprising: de-referencing the reference data structure to identify an audio snippet; and playing the audio snippet via a speaker of a client device, concurrent with the video segment.

13. A method for providing instructional media based on cue points, the method comprising:
  obtaining an instructional media for a cooking instruction describing a plurality of sequential steps for a meal preparation, the instructional media comprising multiple timestamps, multiple media components and a table of contents data structure, wherein the multiple media components include multiple video segments associated with different of the sequential steps for the meal preparation;
  indexing the instructional media according to a plurality of cue points;
  providing a subset of the instructional media to a client device associated with the user;
  obtaining a first user selection of a first cue point associated with a first timestamp and a first step of the cooking instruction;
  rendering a first video segment of the instructional media, wherein the first video segment is associated with the first cue point;
  obtaining a second user selection of a second cue point associated with a second timestamp of the instructional media and a second step of the cooking instruction, where a second video segment is associated with the second cue point and the second timestamp is different from the first timestamp; and
  rendering the first video segment and the second video segment concurrently.

14. The method of claim 13, wherein the subset of the instructional media is selected based on a history of the user.

15. The method of claim 13, wherein the subset of the instructional media is selected based on a personalization option of the user.

16. The method of claim 13, wherein the subset of the instructional media is selected based on a user interface of the client device.

17. The method of claim 13, wherein the subset of the instructional media comprises a link to 3rd party media components associated with the user.

18. The method of claim 13, wherein the instructional media is obtained from a population of users.

* * * * *